(12) United States Patent
Yamauchi et al.

(10) Patent No.: US 9,139,489 B2
(45) Date of Patent: Sep. 22, 2015

(54) METHOD OF MANUFACTURING OLEFIN HAVING 2 TO 4 CARBON ATOMS BY FISCHER-TROPSCH REACTION

(71) Applicants: SUMITOMO CHEMICAL COMPANY, LIMITED, Chuo-ku, Tokyo (JP); KYUSHU UNIVERSITY, NATIONAL UNIVERSITY CORPORATION, Fukuoka-shi, Fukuoka-ken (JP); NATIONAL UNIVERSITY CORPORATION OITA UNIVERSITY, Oita-shi, Oita-ken (JP); National University Corporation University of Toyama, Toyama-shi, Toyama-ken (JP)

(72) Inventors: Miho Yamauchi, Fukuoka (JP); Katsutoshi Nagaoka, Oita (JP); Katsutoshi Sato, Oita (JP); Noritatsu Tsubaki, Toyama (JP); Akihiro Yuasa, Tsukuba (JP); Hideyuki Higashimura, Tsukuba (JP); Takeshi Ishiyama, Tsukuba (JP)

(73) Assignees: SUMITOMO CHEMICAL COMPANY, LIMITED, Tokyo (JP); Kyushu University, NATIONAL UNIVERSITY CORPORATION, Fukuoka-shi (JP); NATIONAL UNIVERSITY CORPORATION OITA UNIVERSITY, Oita-shi (JP); NATIONAL UNIVERSITY CORPORATION UNIVERSITY OF TOYAMA, Toyama-shi (JP)

( * ) Notice: Subject to any disclaimer, the term of this patent is extended or adjusted under 35 U.S.C. 154(b) by 0 days.

(21) Appl. No.: 13/962,088

(22) Filed: Aug. 8, 2013

(65) Prior Publication Data

US 2014/0045955 A1    Feb. 13, 2014

(Continued)

(30) Foreign Application Priority Data

Aug. 10, 2012  (JP) ................................. 2012-178548
Feb. 28, 2013  (JP) ................................. 2013-040105

(51) Int. Cl.
    *C07C 1/04*      (2006.01)
    *B01J 37/03*     (2006.01)

(52) U.S. Cl.
    CPC .............. *C07C 1/0425* (2013.01); *B01J 21/18* (2013.01); *B01J 23/75* (2013.01); *B01J 29/40* (2013.01);
    (Continued)

(58) Field of Classification Search
    CPC   C07C 2523/745; C07C 1/0445; C07C 11/06; C07C 1/0425; B01J 21/18; B01J 2229/183; B01J 23/75; B01J 29/40; B01J 35/0006; B01J 35/0013; B01J 35/002; B01J 35/006; B01J 37/031; B01J 37/035; B01J 37/16; B01J 37/18
    USPC ........................................................ 518/721
    See application file for complete search history.

(56) References Cited

U.S. PATENT DOCUMENTS 4,177,203  A    12/1979  Kolbel et al.

(Continued)

FOREIGN PATENT DOCUMENTS

GB          1 553 361 A    9/1979

(Continued)

OTHER PUBLICATIONS

Machine generated English language translation of JP2010116328, May 27, 2010, pp. 1-35.*

(Continued)

*Primary Examiner* — Jafar Parsa
*Assistant Examiner* — Amy C Bonaparte
(74) *Attorney, Agent, or Firm* — Sughrue Mion, PLLC

(57) ABSTRACT

Provided are a method of manufacturing an olefin having 2 to 4 carbon atoms including: reacting a catalyst with synthesis gas through a Fischer-Tropsch reaction, thereby obtaining the olefin having 2 to 4 carbon atoms, in which the catalyst is a catalyst obtained by reducing the iron ion and the cobalt ion in a dispersion liquid or a solution containing the iron ion, the cobalt ion and a dispersant that interacts with the iron ion and the cobalt ion, and a method of manufacturing propylene, which uses the above manufacturing method.

9 Claims, 2 Drawing Sheets

(51) Int. Cl.
  *B01J 37/16* (2006.01)
  *B01J 37/18* (2006.01)
  *B01J 35/00* (2006.01)
  *B01J 21/18* (2006.01)
  *B01J 23/75* (2006.01)
  *B01J 29/40* (2006.01)

(52) U.S. Cl.
  CPC ............ *B01J 35/002* (2013.01); *B01J 35/0006* (2013.01); *B01J 35/006* (2013.01); *B01J 35/0013* (2013.01); *B01J 37/031* (2013.01); *B01J 37/035* (2013.01); *B01J 37/16* (2013.01); *B01J 37/18* (2013.01); *C07C 1/0445* (2013.01); *B01J 2229/183* (2013.01); *C07C 2523/745* (2013.01)

(56) References Cited

U.S. PATENT DOCUMENTS 4,624,967 A * 11/1986 Fiato et al. .................. 518/700
2009/0226357 A1   9/2009 Uzio et al.
2011/0118365 A1   5/2011 Steiner et al.

FOREIGN PATENT DOCUMENTS

| JP | 56-48491 B2 | | 11/1981 | |
| JP | 2006-297286 A | | 11/2006 | |
| JP | 2009-515693 A | | 4/2009 | |
| JP | 2009-131835 A | | 6/2009 | |
| JP | 2010116328 | * | 5/2010 | ............ B01J 23/002 |

OTHER PUBLICATIONS

Nakamura, Michihiro, et al. Stud. Surf. Sci. Catal. 7, "Fischer-Tropsch Synthesis with Iron-Cobalt Alloy Catalysts" Pt/A, pp. 432-446, 1981.*

Zaman, M., et al. Fuel Processing Technology "Fischer-Tropsch synthesis over cobalt dispersed on carbon nanotube-based supports and activated carbon" 90, 2009, pp. 1214-1219.*

* cited by examiner

METHOD OF MANUFACTURING OLEFIN HAVING 2 TO 4 CARBON ATOMS BY FISCHER-TROPSCH REACTION

BACKGROUND OF THE INVENTION

1. Field of the Invention

The present invention relates to a method of manufacturing an olefin (hereinafter, may be referred to as "a light olefin" or "a light olefin having 2 to 4 carbon atoms") having 2 to 4 carbon atoms using a Fischer-Tropsch reaction.

Priority is claimed on Japanese Patent Application No. 2012-178548, filed on Aug. 10, 2012, and Japanese Patent Application No. 2013-040105, filed on Feb. 28, 2013, the contents of which are incorporated herein by reference.

2. Description of Related Art

As a method of synthesizing hydrocarbons from synthesis gas (i.e., mixed gas containing carbon monoxide and hydrogen as the main components), a Fischer-Tropsch reaction is known. The Fischer-Tropsch reaction may include, for example, a reaction in which straight-chain saturated hydrocarbons are generated from synthesis gas ($CO+H_2$) using a cobalt-based catalyst as a metal catalyst. The reaction formula at this time is as follows.

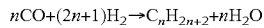

$$nCO+(2n+1)H_2 \rightarrow C_nH_{2n+2}+nH_2O$$

In the related art, the objective product of synthesis of a hydrocarbon from synthesis gas through the FT reaction is a saturated hydrocarbon in most cases. The saturated hydrocarbons are further subjected to various processes such as hydrocracking and isomerization and then are used as fuels or lubricating oils. On the other hand, in the Fischer-Tropsch reaction in which an iron-based catalyst is used, there may be cases where unsaturated hydrocarbons are generated along with the saturated hydrocarbons. However, the selectivity of the saturated hydrocarbons is very low. Therefore, in general, the unsaturated hydrocarbons are converted into saturated hydrocarbons through hydrogenation or the like.

On the other hand, light olefins such as ethylene, propylene, and butene are widely used as raw material compounds in the chemical industry. Particularly, propylene is a useful and important compound as a starting material, for example, in the manufacture of polypropylene.

Hitherto, as the Fischer-Tropsch reaction which aims to manufacture light olefins, a method in which an iron-based catalyst in which a manganese-based compound is contained as a support (refer to Patent Literatures 1 and 2), and a method in which a catalyst which is obtained by carrying iron, copper, and potassium in a silica porous support is used (refer to Patent Literature 3) are disclosed.

CITATION LIST

Patent Literature

[Patent Literature 1] Japanese Examined Patent Application Publication No. S56-48491
[Patent Literature 2] U.S. Pat. No. 4,177,203
[Patent Literature 3] Japanese Unexamined Patent Application, First Publication No. 2006-297286

SUMMARY OF THE INVENTION

However, in the methods disclosed in Patent Literatures 1 to 3, the CO (carbon monoxide) conversion rate is not sufficient, and thus a further improvement on the CO conversion rate is desired in view of practical uses.

The present invention has been made taking the foregoing circumstances into consideration, and an object thereof is to provide a method of manufacturing a light olefin having 2 to 4 carbon atoms using a Fischer-Tropsch reaction catalyst which exhibits a high CO conversion rate, and particularly, a method of manufacturing propylene.

In order to solve the aforementioned problem, the present invention provides a method of manufacturing an olefin having 2 to 4 carbon atoms, including: reacting a catalyst with synthesis gas through a Fischer-Tropsch reaction, thereby obtaining the olefin having 2 to 4 carbon atoms, in which the catalyst is obtained by reducing an iron ion and a cobalt ion in a dispersion liquid or a solution containing the iron ion, the cobalt ion and a dispersant that interacts with the iron ion and the cobalt ion.

In the present invention, it is preferable that a molar ratio of iron and cobalt in the catalyst, which is represented by [mole number of iron]:[mole number of cobalt], be 20:80 to 80:20.

In the present invention, it is preferable that 50% or more of the total number of granular particles of the catalyst have particle diameters of 1 to 50 nm.

In the present invention, it is preferable that the catalyst further include a carbon support.

In the present invention, it is preferable that the Fischer-Tropsch reaction be a gas-phase reaction.

In addition, the present invention provides a method of manufacturing propylene, which uses the above manufacturing method.

According to the present invention, a method of manufacturing a light olefin having 2 to 4 carbon atoms, particularly propylene, using a Fischer-Tropsch reaction with a high CO conversion rate can be provided.

DETAILED DESCRIPTION OF THE INVENTION

<Fischer-Tropsch Reaction Catalyst>

Figure 1:
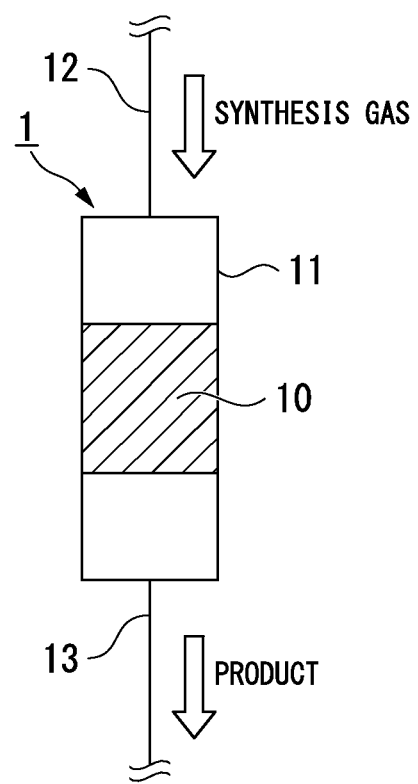
FIG. 1 is a cross-sectional view schematically illustrating an example of a manufacturing apparatus which is appropriately applied to a flow type fixed bed process used in a Fischer-Tropsch reaction.

A Fischer-Tropsch reaction (hereinafter, may be referred to as "FT reaction") catalyst used in the present invention contains alloy particles, and the alloy particles are alloy particles obtained by reducing metal ions (i.e., an iron ion and a cobalt ion) in a dispersion liquid or a solution containing the iron ion and the cobalt ion (hereinafter, may be collectively referred to as "metal ions") and a dispersant that interacts with the metal ions.

When the FT reaction catalyst is manufactured through the aforementioned processes, a high CO conversion rate in the FT reaction can be achieved. In addition, the "CO conversion rate" is calculated by "{[CO consumption amount (mole number)]/[CO supply amount (mole number)]}×100".

The dispersion liquid or the solution may be prepared by blending a metal-containing compound which is an ion source of the metal ions, the dispersant, a solvent, and other components as necessary (for example, a reducing agent, which will be described later).

As the metal-containing compound, those having high water solubility are preferable in terms of ease of removal in a removing method, which will be described later. Examples thereof include a metal-containing inorganic compound such as an acetate salt, a fluoride salt, a chloride salt, a bromide salt, an iodide salt, a sulfate salt, a nitrate salt, and hydrates thereof, and a metal complex such as an acetylacetonate complex. The anion of the nitrate salt is easily removed by heating.

Among these, more preferable examples of the metal-containing compound include the acetate salt, the nitrate salt, and the acetylacetonate complex.

Specific examples of the metal-containing compound include iron acetate, cobalt acetate, and iron(III) acetylacetonate.

The dispersant prevents the aggregation of the generated alloy particles in the dispersion liquid or the solution (that is, a reaction liquid) during the reduction reaction or after the reduction reaction. Since the aggregation of the alloy particles is prevented, the sizes (particle diameter and the like) thereof can be controlled. For example, by increasing the amount (mass) of the dispersant in the dispersion liquid or the solution with respect to the amount (mass) of the metal ions, the particle diameter of the alloy particles can be reduced. In order to reduce the particle diameter of the alloy particles, the amount of the metal ions in the dispersion liquid or the solution may be reduced with respect to the amount of the dispersant. In addition, by increasing the molecular weight of the dispersant in the dispersion liquid or the solution, the particle diameter of the alloy particles can also be reduced.

The dispersant may be appropriately selected depending on the type of the alloy particles and the like. However, in terms of ease of removal in the removing method, which will be described later, those having high solubility in a polar solvent are preferable, those having high water solubility are more preferable, and a polymer is preferable due to its excellent dispersant effect.

Among the dispersants, examples of a water-soluble polymer include a polymer having an alkylene ether structure such as polyethylene glycol (PEG) and polypropylene glycol; polyvinyl alcohol; polyvinyl ether; polyacrylate; polyvinylpyrrolidone (PVP); poly(mercaptomethylenestyrene-N-vinyl-2-pyrrolidone); and polyacrylonitrile.

The weight average molecular weight of the dispersant in terms of PEG equivalent value is preferably 300 to 10,000, more preferably 500 to 8000, even more preferably 700 to 5000, and particularly preferably 1000 to 3000, in terms of easily controlling the particle diameter and the particle diameter distribution of the alloy particles.

In this specification, the "dispersion liquid" is a mixture in which a blended material containing an iron ion, a cobalt ion, the dispersion that interacts with the iron ion and the cobalt ion, and a solvent described below are not completely dissolved but dispersed. On the other hand, the "solution" is a mixture in which a blended material containing an iron ion, a cobalt ion, the dispersion that interacts with the iron ion and the cobalt ion, and a solvent described below are dissolved. The solvent used for preparing the dispersion liquid or the solution is not particularly limited as long as it does not impede the reduction reaction. As the solvent, water; and alcohols such as 1,2-ethanediol (ethylene glycol), 1,2-propanediol, 1,3-propanediol, 1,2-butanediol, 1,3-butanediol, 1,4-butanediol, 2,3-butanediol, pentanediol, hexanediol, heptanediol, octanediol, diethylene glycol, triethylene glycol, tetraethylene glycol, dipropylene glycol, hexylene glycol, 2-butene-1,4-diol, glycerol, 1,1,1-trishydroxymethylethane, 2-ethyl-2-hydroxymethyl-1,3-propanediol, 1,2,3-hexanetriol, and benzyl alcohol are preferable, 1,2-ethanediol, 1,2-propanediol, 1,3-propanediol, and triethylene glycol are more preferable, and triethylene glycol is particularly preferable.

The solvents may be used singly or in a combination of two or more types thereof.

The other components are arbitrary components blended as necessary, and examples thereof include coexistent components that coexist with the alloy particles in the FT reaction catalyst, which will be described later.

A method of blending the components to prepare the dispersion liquid or the solution is not particularly limited, and the components may be mixed while being sequentially added or the components may be mixed after adding all the components. In a case of mixing the components while being sequentially added, the addition order thereof is not particularly limited as long as the blended components can be uniformly dispersed or dissolved. For example, a liquid in which the dispersant is dispersed or dissolved and a solution in which the remaining components such as the metal-containing compound may be appropriately mixed for the preparation.

The method of mixing the components is not particularly limited, and for example, a conventional method using a stirrer, a stirring blade, and the like may be applied.

When the concentrations of the dispersant and the metal ions in the dispersion liquid or the solution are too high, an effect of suppressing the aggregation of the alloy particles is deteriorated. Here, the concentration of the dispersant in the dispersion liquid or the solution is, with respect to the total mass of the dispersion liquid or the solution, preferably $1\times10^{-4}$ to 5% by mass, and more preferably $1\times10^{-3}$ to 0.5% by mass. The concentration of the metal ions in the dispersion liquid or the solution is, with respect to the total mass of the dispersion liquid or the solution, preferably $3\times10^{-7}$ to 1% by mass, and more preferably $1\times10^{-7}$ to 0.1% by mass.

The metal ions are reduced by a reducing agent in the dispersion liquid or the solution. The reducing agent may be blended in the dispersion liquid or the solution in advance, or may be blended after preparing the dispersion liquid or the solution.

The reducing agent may be a conventional agent, and examples thereof include sodium borohydride ($NaBH_4$), potassium borohydride ($KBH_4$), sodium triethylborohydride ($Na(CH_3CH_2)_3BH$), potassium triethylborohydride ($K(CH_3CH_2)_3BH$), sodium cyanoborohydride ($NaBH_3CN$), lithium borohydride ($LiBH_4$), lithium triethylborohydride ($LiBH(CH_2CH_3)_3$), and triethylsilane ($(CH_3CH_2)_3SiH$).

The reducing agents may be used singly or in a combination of two or more types thereof.

The amount of the reducing agent blended is, with respect to 1 mol of the metal ions, preferably 0.1 mol or higher, and more preferably 1 mol or higher. Specifically, the amount of the reducing agent blended is, with respect to 1 mol of the metal ions, preferably 0.1 mol or higher and 100 mol or less, and more preferably 1 mol or higher and 50 mol or less.

The reaction temperature during the reduction is preferably 20 to 200° C., and more preferably 60 to 150° C. The reaction time for the reduction is preferably 1 to 120 minutes, and more preferably 3 to 30 minutes.

The alloy particles comprise iron and cobalt as the constituent elements, and preferably consist essentially of iron and cobalt as the constituent elements in order to obtain a FT reaction catalyst having more excellent activity.

In the alloy particles made of iron and cobalt, in terms of further increasing the CO conversion rate in the FT reaction, the molar ratio of iron and cobalt, which is represented by [mole number of iron]:[mole number of cobalt], is preferably 20:80 to 80:20, more preferably 30:70 to 70:30. In terms of further increasing the selectivity of propylene, a molar ratio of 40:60 to 60:40 is preferable. In addition, the "selectivity of propylene" can be calculated with the value of a peak area percentage in a spectrum obtained by analyzing the reaction products using gas chromatography.

In the FT reaction catalyst, the alloy particles having particle diameters of 1 to 50 nm preferably occupy 50% or more of the total number of alloy particles, those having particle diameters of 3 to 40 nm more preferably occupy 50% or more of the total number of alloy particles, those having particle diameters of 10 to 40 nm even more preferably occupy 50% or more of the total number of alloy particles, those having particle diameters of 10 to 40 nm especially preferably occupy 70% or more of the total number of alloy particles, and those having particle diameters of 10 to 40 nm particularly preferably occupy 90% or more of the total number of alloy particles.

More specifically, in the FT reaction catalyst, the alloy particles having particle diameters of 1 to 50 nm preferably occupy 50% or more and 100% or less of the total number of alloy particles, those having particle diameters of 3 to 40 nm more preferably occupy 50% or more and 100% or less of the total number of alloy particles, those having particle diameters of 10 to 40 nm even more preferably occupy 50% or more and 100% or less of the total number of alloy particles, those having particle diameters of 10 to 40 nm especially preferably occupy 70% or more and 100% or less of the total number of alloy particles, and those having particle diameters of 10 to 40 nm particularly preferably occupy 90% or more and 100% or less of the total number of alloy particles.

The particle diameter of the alloy particles may be determined by TEM measurement Here, the "particles" are primary particles.

In the reduction reaction, an acid derived from the metal-containing compound may be generated, and thus a base for neutralization may be added to the dispersion liquid or the solution before the reduction reaction or during the reduction reaction.

The base is not particularly limited, and preferable examples thereof include sodium hydroxide and potassium hydroxide.

The amount of the base used may be appropriately controlled so that the pH of the reaction liquid can be adjusted to a target value.

A crude product obtained by the reduction reaction is preferably washed with a washing solvent and purified. In this method, a redundant dispersant and impurities such as metal ions can be removed simultaneously.

The washing solvent is not particularly limited, and acetone, diethyl ether, water, methanol, ethanol and isopropanol are preferable due to their ability to dissolve the dispersant and the metal ions and a high effect in removal thereof.

The washing solvents may be used singly or in a combination of two or more types thereof.

It is preferable that the alloy particles after the washing be further subjected to a heating treatment.

The heating treatment may be performed, for example, under the vacuum condition, or in the presence of inert gas such as argon gas and nitrogen gas. Temperature during the heating treatment is preferably 300 to 1500° C., more preferably 400 to 1200° C., and even more preferably 600 to 1000° C. In addition, during the heating treatment, a metal reduction treatment may be also performed using hydrogen gas.

The obtained alloy particles may further be subjected to a purifying treatment by a conventional method.

The FT reaction catalyst used in the present invention contains the alloy particles, and may be made of only the alloy particles or may contain coexistent components in addition to the alloy particles.

Examples of the coexistent component include a support which supports the alloy particles.

Examples of the material of the support include silica, alumina, titania, zirconia, ceria, magnesium oxide, zinc oxide and carbon, and alumina, titania, zirconia, ceria and carbon are preferable. Among these, the support is particularly preferably a carbon support.

Among various carbon supports, a particulate carbon support is preferable due to its low cost and large surface area, and carbon black such as Vulcan (registered trademark) and Ketjen Black (registered trademark) or activated carbon is more preferable.

The particle diameter of the support is not particularly limited, and is preferably 10 nm to 100 µm, more preferably 10 nm to 50 µm, even more preferably 20 nm to 500 nm, and particularly preferably 20 nm to 200 nm.

The amount of the alloy particles of the FT reaction catalyst is not particularly limited as long as the FT reaction catalyst has a good catalytic ability, and is preferably 1 to 99% by mass, more preferably 3 to 97% by mass, and even more preferably 5 to 95% by mass, with respect to the total mass of the catalyst.

In addition, the amount of the support of the FT reaction catalyst is not particularly limited as long as the FT reaction catalyst has a good catalytic ability, and is preferably 1 to 99% by mass, more preferably 3 to 97% by mass, and even more preferably 5 to 95% by mass, with respect to the total mass of the catalyst.

The FT reaction catalyst preferably contains a predetermined amount or more of the alloy particles. Specifically, the amount of the alloy particles is preferably 5% by mass or higher, and more preferably 10% by mass or higher with respect to the total mass of the catalyst.

In the case where the FT reaction catalyst contains coexistent components in addition to the alloy particles, the FT reaction catalyst may be manufactured by appropriately blending the alloy particles with the coexistent components.

In addition, as described above, when the alloy particles is prepared, by blending the coexistent components with the metal ions, the dispersant and the solvent, and performing the reduction reaction in the presence of the coexistent components, the FT reaction catalyst may also be manufactured. Even in this case, the same purifying method as described above can be applied.

The FT reaction catalyst used in the present invention causes the CO conversion rate to be high and causes the objective product to be efficiently obtained in a case of being applied to the manufacture of the light olefin having 2 to 4 carbon atoms such as ethylene, propylene, butene through the FT reaction. The catalyst enables the CO conversion rate to be preferably 30% or higher, and more preferably 35% or higher.

In addition, the FT reaction catalyst used in the present invention is appropriate for the manufacture of propylene particularly using the FT reaction. For example, by controlling the composition of metals constituting the alloy particles, the selectivity of propylene in the FT reaction can be 14% or higher.

<Method of Manufacturing Light Olefin Having 2 to 4 Carbon Atoms>

The method of manufacturing an olefin having 2 to 4 carbon atoms according to the present invention is a method of manufacturing an olefin having 2 to 4 carbon atoms in which an olefin having 2 to 4 carbon atoms is obtained by reacting the catalyst with synthesis gas through the Fischer-Tropsch reaction. As the catalyst, a catalyst is used which is obtained by reducing the iron ion and the cobalt ion in a dispersion liquid or a solution containing the iron ion, the cobalt ion, and a dispersant that interacts with the iron ion and the cobalt ion. The method of manufacturing a light olefin having 2 to 4 carbon atoms according to the present invention is particularly appropriate for a method of manufacturing propylene, uses the FT reaction catalyst, and employs the FT reaction.

In the manufacturing method, the FT reaction is preferably a gas-phase reaction, and a flow type fixed bed process is preferably employed as a single-stage reaction process.

In addition, in the present specification, as the olefin having 2 to 4 carbon atoms, specifically, there are ethylene, propylene, 1-butene, 2-butene, isobutene and 1,3-butadiene.

FIG. 1 is a cross-sectional view schematically illustrating an example of a manufacturing apparatus which is appropriately applied to the flow type fixed bed process.

In the manufacturing apparatus 1 illustrated in FIG. 1, in a region of a part of the inside of a cylindrical reactor 11, in a central axis direction of (a gas flow direction), a FT reaction catalyst 10 is held over the entire area of the reactor 11 in the radial direction (in a direction perpendicular to the central axis). A first pipe 12 is connected to the upper portion of the reactor 11, and a second pipe 13 is connected to the lower portion of the reactor 11.

In a case of using the manufacturing apparatus 1, synthesis gas (mixed gas containing carbon monoxide (CO) and hydrogen ($H_2$) as the main components) is supplied to the inside of the reactor 11 through the first pipe 12. Here, by appropriately controlling the temperature and the pressure of the inside of the reactor 11, a product (gas containing a light olefin having 2 to 4 carbon atoms) is generated, and the product is taken out of the reactor 11 from the second pipe 13 along with unreacted synthesis gas. In addition, the manufacturing apparatus 1 is an example which is appropriate for the manufacture of the light olefin having 2 to 4 carbon atoms, and the manufacturing apparatus is not limited thereto.

The FT reaction catalyst obtained by the manufacturing method described above may be used as it is, or may also be used after being subjected to any treatment such as pulverization, molding, and granulating in advance.

The FT reaction catalyst may be reduced before the use either under a hydrogen gas atmosphere at normal pressure to 10 MPa or under a synthesis gas atmosphere at normal pressure to 10 MPa, at 200 to 450° C. for 1 to 72 hours to be activated. The activation treatment is generally performed in the art, and is recommended for efficient activation. In addition, in the synthesis gas, the molar ratio of hydrogen relative to carbon monoxide, which is represented by [mole number of hydrogen]/[mole number of carbon monoxide], is preferably 0.5 to 5, and more preferably 0.5 to 2.

The reaction temperature during the FT reaction is preferably 200 to 400° C., and more preferably 250 to 350° C. In addition, the reaction pressure during the FT reaction is preferably normal pressure to 10 MPa, more preferably 0.1 to 10 MPa, and particularly preferably 0.3 to 5 MPa.

In addition, the reaction time during the FT reaction may be controlled according to the other reaction conditions, and from the viewpoint of stabilizing catalysis, is preferably 3 hours or longer, and more preferably 4 hours or longer.

The ratio (W/F) of the catalyst weight (W) (g) relative to the supply rate of the synthesis gas (F) (mol/h) is preferably 0.1 to 100 g·h/mol, and more preferably 1.0 to 50 g·h/mol.

As the synthesis gas, gas containing hydrogen and carbon monoxide, gas containing hydrogen and carbon dioxide, and the like may be used. Among these, the total amount of hydrogen and carbon monoxide in the synthesis gas is preferably 50 volume % or higher of the entire amount of the synthesis gas. Specifically, the total amount of hydrogen and carbon monoxide is preferably 50 volume % or higher and 100 volume % or less of the entire amount of the synthesis gas. Since the synthesis gas is used, the productivity of the light olefin is further increased.

In the synthesis gas, since the hydrogenation reaction of carbon monoxide easily proceeds and the productivity of the light olefin is further increased, the molar ratio of hydrogen relative to carbon monoxide, which is represented by [mole number of hydrogen]/[mole number of carbon monoxide], is preferably higher than 0.3.

In addition, in the synthesis gas, in order to suppress the deterioration in the productivity of the light olefin due to a too small amount of carbon monoxide, the molar ratio of hydrogen relative to carbon monoxide, which is represented by [mole number of hydrogen]/[mole number of carbon monoxide], is preferably 3 or less.

Here, in the synthesis gas, the molar ratio of hydrogen relative to carbon monoxide, which is represented by [mole number of hydrogen]/[mole number of carbon monoxide], is more preferably 0.5 to 3, even more preferably 0.5 to 2.5, and particularly preferably 0.6 to 2.

In addition, a hydrocarbon compound generated by the FT reaction can further increase the amount of the light olefin having 2 to 4 carbon atoms because the hydrogen compound is subjected to cracking treatment in the presence of a zeolite catalyst.

As the zeolite catalyst, any of natural and synthetic zeolites may be used, and ZSM-5 is preferably used. Particularly, in the ZSM-5, the molar ratio of $SiO_2$ and $Al_2O_3$, which is represented by "$SiO_2/Al_2O_3$", is preferably 50 to 4000, more preferably 90 to 1000, and particularly preferably 200 to 800.

In addition, acidic properties and durability such as acid strength and density of the zeolite catalyst can be enhanced by treating the zeolite catalyst with a phosphorus-containing compound, a lanthanum-containing compound, an alkaline earth metal-containing compound, a transition metal-containing compound, and the like.

The ZSM-5 contains at least one type selected from the group consisting of an alkali metal, an alkaline earth metal and a transition metal, and only a single type or two or more types of the alkali metal, the alkaline earth metal, and the transition metal may be contained.

In the ZSM-5, with respect to the total mass of the ZSM-5, the total amount of the alkali metal, the alkaline earth metal and the transition metal is preferably 0.01 to 30% by mass, more preferably 0.05 to 20% by mass, and particularly preferably 0.1 to 10% by mass.

The alkali metal is preferably lithium, sodium, potassium, rubidium or cesium.

The alkaline earth metal is preferably beryllium, magnesium, calcium, strontium or barium, more preferably magnesium, calcium, strontium or barium, even more preferably magnesium, calcium or barium, and particularly preferably calcium or barium.

The transition metal is preferably a d-block element, more preferably scandium, titanium, vanadium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum or gold, even more preferably vanadium, manganese, iron, cobalt, copper, niobium, molybdenum, silver, tantalum or tungsten, particularly preferably manganese, iron, cobalt, copper or silver, particularly especially manganese or silver, and most preferably manganese.

Among the alkali metal, the alkaline earth metal and the transition metal, the ZSM-5 preferably contains the alkaline earth metal.

As a method in which the alkali metal, the alkaline earth metal and the transition metal (hereinafter, may be referred to as "alkali metal and the like") are introduced in the ZSM-5, there is a method in which the alkali metal and the like are introduced to a zeolite which is a raw material (in order to distinguish from the zeolite catalyst used in the cracking treatment, hereinafter, may be referred to as "raw material zeolite") in accordance with a typical method such as an impregnation method and an ion exchange method. However, there is also a method in which simultaneously with the manufacture of a zeolite, the alkali metal and the like are introduced to the zeolite (hereinafter, may be referred to as "a method in which the alkali metal and the like are introduced during manufacturing a zeolite"). Here, the "raw material zeolite" means a typical zeolite, and also includes one that can be used for the cracking treatment in the present invention. In addition, "the alkali metal and the like are introduced during manufacturing a zeolite" means that in the manufacturing process of the zeolite, during forming main skeletons constituted by silicon, aluminum and oxygen, the alkali metal and the like are introduced between the main skeletons.

Among these, in the present invention, the ion exchange method or the method in which the alkali metal and the like are introduced during manufacturing the zeolite is preferable, the method in which the alkali metal and the like are introduced during manufacturing the zeolite is preferable in terms of introducing metals more uniformly, and the ion exchange method is preferable in terms of simply using a commercially available zeolite as the raw material zeolite.

In addition, the molar ratio of the elements constituting the zeolite catalyst can be obtained by the inductively coupled plasma emission spectrometry (hereinafter, may be referred to as "ICP analysis").

A method of manufacturing the zeolite catalyst will now be described.

The zeolite catalyst can be manufactured by putting a mixture of a silicon source, an aluminum source, a structure regulating agent, and an introduced element source as necessary, in a pressure-resistant container, and reacting the mixture at a predetermined temperature for a predetermined time (for example, at 100 to 250° C. and for 1 to 150 hours). In addition, the zeolite catalyst can also be manufactured by putting a dried gel obtained by removing water from aforementioned the mixture in a pressure-resistant container so as to be allowed not to come into contact with water or water containing a structure regulating agent, and supplying steam thereto so as to react with the resultant. Those obtained may also be continuously subjected to a calcination treatment at a predetermined temperature for a predetermined time (for example, at 300 to 800° C. for 1 to 48 hours). The silicon source, the aluminum source, the structure regulating agent and the introduced element source may be used singly or in a combination of two or more types thereof.

The silicon source is a compound containing silicon, and means a raw material that can be a constituent component of the zeolite catalyst. The silicon source is not particularly limited as long as it can be a constituent component of a zeolite, examples thereof include tetraalkyl orthosilicate, silica, silica gel, thermally decomposed silica, precipitated silica, colloidal silica, water glass, wet-type silica, amorphous silica, fumed silica, sodium silicate, kaolinite, diatomite and aluminum silicate, and tetraalkyl orthosilicate and fumed silica are preferable.

The aluminum source is a compound containing aluminum, and means a raw material that can be a constituent component of the zeolite catalyst. The aluminum source is not particularly limited as long as it can be a constituent component of a zeolite, examples thereof include aluminate, aluminum oxide, boehmite, aluminum oxyhydroxide, aluminum hydroxide, aluminum salts (aluminum chloride, aluminum nitrate, aluminum sulfate, and the like), aluminum alkoxides (aluminum isopropoxide, and the like), alumina white, and aluminum fluoride, and aluminum nitrate and aluminum oxide are preferable.

The structure regulating agent is a compound for determining the structure of the zeolite. The structure regulating agent is not particularly limited and may use a conventional agent, and examples thereof include an organic base such as a quaternary ammonium compound and amine. Examples of the organic base include hydroxide salts, phosphate salts, fluoride salts, chloride salts, bromide salts, and acetate salts of tetramethylammonium, tetraethylammonium, tetrapropylammonium, tetra-n-butylammonium, benzyltrimethylammonium, 3-(trifluoromethyl)phenyltrimethylammonium, and n-hexadecyltrimethyl ammonium; dipropylamine; triethylamine; cyclohexylamine; 1-methylimidazole; morpholine; pyridine; piperidine. Among these, diethyl ethanolamine, tetramethylammonium hydroxide, tetraethylammonium hydroxide, tetrapropylammonium hydroxide, tetra-n-butyl ammonium hydroxide, benzyltrimethylammonium hydroxide, dipropylamine, triethylamine, morpholine, pyridine and piperidine are preferable, tetramethylammonium hydroxide, tetraethylammonium hydroxide, tetrapropylammonium hydroxide, tetra-n-butylammonium hydroxide and benzyltrimethylammonium hydroxide are more preferable, and tetrapropylammonium hydroxide is even more preferable.

The introduced element source is a compound which contains an element (for example, in a case of the ZSM-5, one or more types selected from the group consisting of an alkali metal, an alkaline earth metal and a transition metal) to be introduced between the main skeletons of the zeolite catalyst, means a material which does not correspond to the silicon source, the aluminum source, and structure regulating agent, and which can be a constituent component of the zeolite catalyst. As the method of manufacturing the zeolite catalyst using the introduced element source, a method of introducing the alkali metal and the like during manufacturing the zeolite described above can be applied.

The introduced element source is not particularly limited as long as it can be a constituent component of a zeolite. Examples thereof include metal salts, metal complexes, and more specifically include carbonate salts, nitrate salts, nitrite salts, sulfate salts, sulfite salts, acetate salts, formate salts, phosphate salts, hydrogen phosphate salts, dihydrogen phosphate salts, fluoride salts, chloride salts, bromide salts, iodide salts, hydroxide salts, and acetylacetonate complexes of metal elements. Among these, the introduced element source is preferably a nitrate salt or an acetate salt of a metal element in terms of ease of removal of anions through heating.

The metals of the introduced element source are preferably one or more types selected from the group consisting of alkaline earth metals and transition metals. The alkaline earth metals contained in the introduced element source are preferably beryllium, magnesium, calcium, strontium and barium, more preferably magnesium, calcium, strontium and barium, even more preferably magnesium, calcium, and barium and particularly preferably calcium and barium. The transition metals in the introduced element source are preferably d-block elements, more preferably scandium, titanium, vanadium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum or gold, even more preferably vanadium, manganese, iron, cobalt, copper, niobium, molybdenum, silver, tantalum or tungsten, particularly preferably manganese, iron, cobalt, copper or silver, especially preferably manganese or silver, and most preferably manganese.

Metals contained in the introduced element source are preferably alkaline earth metals.

Specific examples of the introduced element source are preferably copper acetate, copper nitrate, manganese acetate, manganese nitrate, barium acetate, barium nitrate, calcium acetate and calcium nitrate, and more preferably barium acetate, barium nitrate, calcium acetate and calcium nitrate.

The zeolite catalyst obtained by the manufacturing method further contains one or more types selected from the group consisting of the alkali metal, the alkaline earth metal and the transition metal by the impregnation method, the ion exchange method, and the like, and may be another zeolite catalyst other than the aforementioned ZSM-5.

Since the zeolite catalyst is likely to be affected by performance deterioration due to carbon deposition caused by an increase in the particle diameter, and thus the particle diameter thereof is preferably 3 μm or less, and more preferably 0.01 to 2.0 μm. Here, the "particle diameter of the zeolite catalyst" means an average value of major axis diameters in the crystals of 50 zeolite catalysts. In addition, the particle diameter may be determined by, for example, a scanning electron microscope (SEM).

The zeolite catalyst may be used after being appropriately subjected to any treatment such as pulverization, molding, granulating, and the like in advance.

In the cracking treatment of the hydrocarbon compound generated by the FT reaction in the presence of the zeolite catalyst, the reaction temperature during the cracking treatment is preferably 300 to 800° C., and more preferably 400 to 650° C.

In addition, the reaction pressure during the cracking treatment is preferably 0.01 to 1 MPa, more preferably 0.01 to 0.5 MPa, and particularly preferably 0.05 to 0.2 MPa.

In addition, the gas space rate during the cracking process is preferably 300 to 30,000 GHSV.

Figure 2:
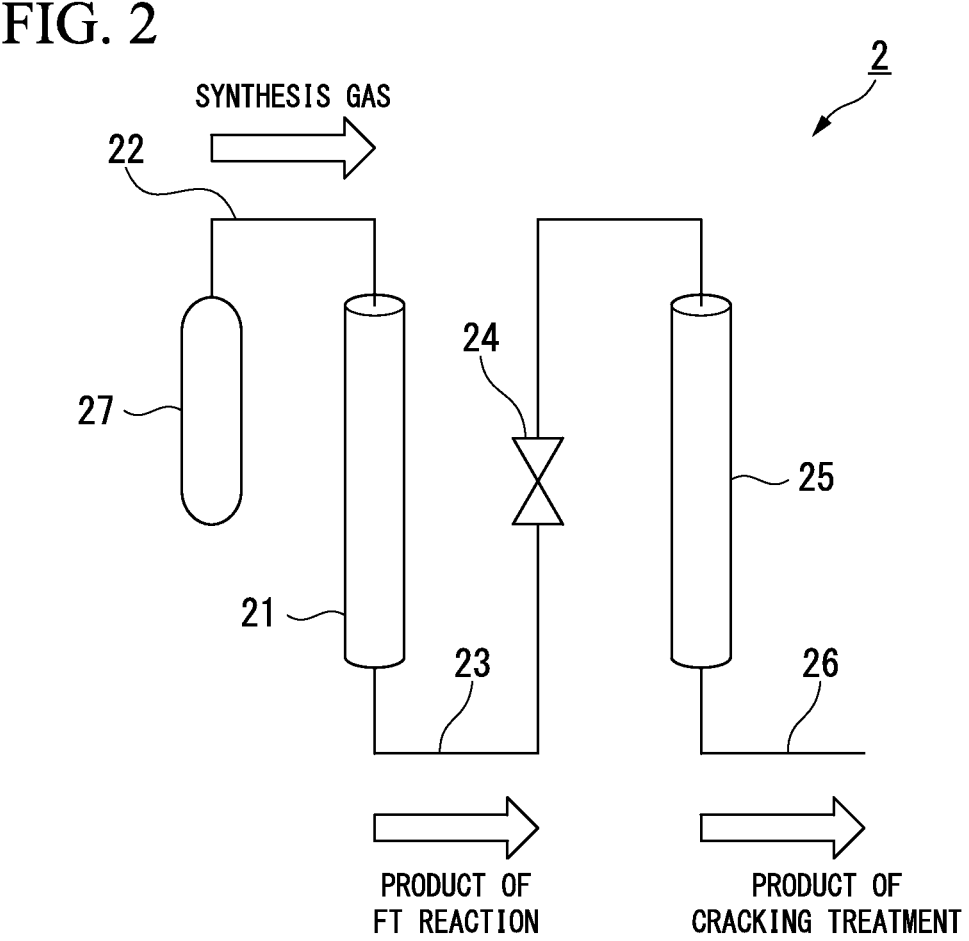
FIG. 2 is a schematic diagram of an example of a manufacturing apparatus which is appropriately applied to a process of performing a cracking treatment on a product of the Fischer-Tropsch reaction in the presence of a zeolite catalyst.

A process in a case where a product of the FT reaction is subjected to the cracking treatment in the presence of the zeolite catalyst will be described with reference to FIG. 2. FIG. 2 is a schematic diagram of an example of a manufacturing apparatus which is appropriately applied to the process of performing the cracking treatment.

The manufacturing apparatus 2 illustrated in FIG. 2 is schematically configured so that a first reactor 21 for performing the FT reaction and a second reactor 25 for performing the cracking treatment are connected to each other via a second pipe 23, a back pressure valve 24 is provided in the middle of the second pipe 23, the upstream side of the first reactor 21 is connected to synthesis gas supply means 27 via a first pipe 22, and the downstream side of the second reactor 25 is connected to a third pipe 26. The first reactor 21, the first pipe 22, and the second pipe 23 respectively correspond to the reactor 11, the first pipe 12, and the second pipe 13 in the manufacturing apparatus 1 of FIG. 1. In addition, although not illustrated here, a cold trap for supplementing a liquid product may be appropriately installed at a necessary place.

In a case of using the manufacturing apparatus 2, after supplying the synthesis gas into the first reactor 21 via the first pipe 22 by using the synthesis gas supply means 27 and conducting the FT reaction, the obtained product of the FT reaction (gas containing the hydrocarbon compound) is supplied into the second reactor 25 via the second pipe 23 and subjected to cracking treatment, thereby generating gas containing a light olefin having 2 to 4 carbon atoms. The gas is taken out from the second reactor 25 through the third pipe 26. The internal pressures of both the first reactor 21 and the second reactor 25 are adjusted by using the back pressure valve 24. In addition, the manufacturing apparatus 2 is an example appropriate for the manufacture of the light olefin having 2 to 4 carbon atoms, and the manufacturing apparatus in a case where the FT reaction and the cracking treatment are performed in combination is not limited thereto.

In the manufacturing method in which the FT reaction and the cracking treatment are performed in combination, the amount of the olefin having 2 to 4 carbon atoms, particularly, propylene in the product can be further increased.

EXAMPLES

Hereinafter, the present invention will be described in more detail according to specific examples. However, the present invention is not limited to the following examples. In addition, the measurement of the particle diameter of the alloy particles and the measurement of the molar ratio of the metals contained in the alloy particles were performed by the following methods.

(Measurement of Particle Diameter of Alloy Particles)

Using a transmission electron microscope (TEM) (JEM-2100F manufactured by JEOL Ltd.), image data of the alloy particles was obtained, and the average particle diameter and the particle diameter distribution were estimated based on the image date of 200 alloy particles.

(Measurement of Molar Ratio of Metals in Alloy Particles)

ICP emission spectroscopy (ICPE-9000 manufactured by Shimadzu Corporation) was performed on the alloy particles by the following method, and the molar ratio of the metals is obtained from the analysis value thereof.

Manufacture of FT Reaction Catalyst

Manufacture Example 1

0.135 g of iron(II) acetate, 0.4 g of cobalt(II) acetate, 1.33 g of polyethylene glycol (polyethylene glycol #1,540 manufactured by NACALAI TESQUE, INC., hereinafter, referred to as "PEG"), and 0.71 g of Vulcan (registered trademark) were mixed with 200 ml of triethylene glycol (hereinafter, referred to as "TEG"). After heating the mixed solution to 120° C., 1.1 g of $NaBH_4$ was added thereto and stirred for 5 minutes, and the resultant was allowed to cool. A mixed solution of acetone and diethyl ether at a ratio of acetone: diethyl ether=2:1 was added to the obtained reaction mixture until the mixture was separated into a black layer and a colorless and transparent solution layer, followed by centrifugation, thereby obtaining a black sample. The obtained black precipitate was dispersed in water. An operation of adding acetone to the mixture to be separated into a black sample and a colorless and transparent solution again and performing centrifugation of the resultant was repeated three times, thereby obtaining a black sample. The sample is called a catalyst precursor. The catalyst precursor was dried in a vacuum desiccator.

The dried catalyst precursor was pulverized to powder. 500 mg of the precursor powder was moved to a quartz boat, and the temperature thereof was raised to 700° C. in a state where 5% $H_2$—Ar gas was flowed, thereby manufacturing a catalyst.

From the result of the TEM measurement, it was confirmed that the particle diameter of Fe—Co nanoparticles supported in Vulcan (registered trademark) was 17±8 nm. From the result of the powder XRD measurement, it was confirmed that the nanoparticles in the manufactured catalyst had a bcc structure. From the result of the ICP-AES measurement, it was confirmed that 14.1 wt % of metals was contained in the catalyst and Fe:Co (molar ratio) was 22:78.

Manufacture Example 2

0.26 g of iron(III) acetylacetonate, 0.27 g of cobalt(II) acetate, 1.33 g of PEG and 0.71 g of Vulcan (registered trademark) were mixed with 200 ml of TEG. After heating the mixed solution to 80° C., 1.1 g of $NaBH_4$ was added thereto and stirred for 5 minutes, and the resultant was allowed to cool. A mixed solution of acetone and diethyl ether at a ratio of acetone:diethyl ether=2:1 was added to the obtained reaction mixture until the mixture was separated into a black layer and a colorless and transparent solution layer, followed by centrifugation, thereby obtaining a black sample. The obtained black precipitate was dispersed in water. An operation of adding acetone to the mixture to be separated into a black sample and a colorless and transparent solution again and performing centrifugation of the resultant was repeated three times, thereby obtaining a black sample. The sample is called a catalyst precursor. The catalyst precursor was dried in a vacuum desiccator.

The dried catalyst precursor was pulverized to powder. 500 mg of the precursor powder was moved to a quartz boat, and the temperature thereof was raised to 700° C. in a state where 5% $H_2$—Ar gas was flowed, thereby manufacturing a catalyst.

From the result of the TEM measurement, it was confirmed that the particle diameter of Fe—Co nanoparticles supported in Vulcan (registered trademark) was 24±14 nm. From the result of the powder XRD measurement, it was confirmed that the nanoparticles in the manufactured catalyst had a bcc structure. From the result of the ICP-AES measurement, it was confirmed that 12.7 wt % of metals were contained in the catalyst and Fe:Co (molar ratio) was 55:45.

Manufacture Example 3

0.39 g of iron(II) acetate, 0.13 g of cobalt(II) acetate, 1.33 g of PEG, and 0.71 g of Vulcan (registered trademark) were mixed with 200 ml of TEG. After heating the mixed solution to 120° C., 1.1 g of $NaBH_4$ was added and stirred for 5 minutes, and the resultant was allowed to cool.

A mixed solution of acetone and diethyl ether at a ratio of acetone:diethyl ether=2:1 was added to the obtained reaction mixture until the mixture was separated into a black layer and a colorless and transparent solution layer, followed by centrifugation, thereby obtaining a black sample. The obtained black precipitate was dispersed in water. An operation of adding acetone to the mixture to be separated into a black sample and a colorless and transparent solution again and performing centrifugation of the resultant was repeated three times, thereby obtaining a black sample. The sample is called a catalyst precursor. The catalyst precursor was dried in a vacuum desiccator.

The dried catalyst precursor was pulverized to powder. 500 mg of the precursor powder was moved to a quartz boat, and the temperature thereof was raised to 700° C. in a state where 5% $H_2$—Ar gas was flowed, thereby manufacturing a catalyst.

From the result of the TEM measurement, it was confirmed that the particle diameter of nanoparticles supported in Vulcan (registered trademark) was 18±9 nm. From the result of the powder XRD measurement, it was confirmed that the nanoparticles in the manufactured catalyst had a bcc structure. From the result of the ICP-AES measurement, it was confirmed that 22 wt % of metals were contained in the catalyst and Fe:Co (molar ratio) was 72:28.

Manufacture Example 4

0.53 g of cobalt(II) acetate, 1.33 g of PEG, and 0.71 g of Vulcan (registered trademark) were mixed with 200 ml of TEG. After heating the mixed solution to 120° C., 1.1 g of $NaBH_4$ was added and stirred for 5 minutes, and the resultant was allowed to cool. A mixed solution of acetone and diethyl ether at a ratio of acetone:diethyl ether=2:1 was added to the obtained reaction mixture until the mixture was separated into a black layer and a colorless and transparent solution layer, followed by centrifugation, thereby obtaining a black sample. The obtained black precipitate was dispersed in water. An operation of adding acetone to the mixture to be separated into a black sample and a colorless and transparent solution again and performing centrifugation of the resultant was repeated three times, thereby obtaining a black sample. The sample is called a catalyst precursor. The catalyst precursor was dried in a vacuum desiccator.

The dried catalyst precursor was pulverized to powder. 500 mg of the precursor powder was moved to a quartz boat, and the temperature thereof was increased to 600° C. in a state where 5% $H_2$—Ar gas was flowed, thereby manufacturing a catalyst.

From the result of the TEM measurement, it was confirmed that the particle diameter of Fe—Co nanoparticles supported in Vulcan (registered trademark) was 28±11 nm. From the result of the powder XRD measurement, it was confirmed that the nanoparticles in the manufactured catalyst had a bcc structure. From the result of the ICP-AES measurement, it was confirmed that 19.3 wt % of Co was contained in the catalyst.

Manufacture Example 5

1 g of iron(III) acetylacetonate, 1.3 g of PEG, and 0.71 g of Vulcan (registered trademark) were mixed with 200 ml of TEG. After heating the mixed solution to 80° C., 1.1 g of $NaBH_4$ was added and stirred for 5 minutes, and the resultant was allowed to cool. A mixed solution of acetone and diethyl ether at a ratio of acetone:diethyl ether=2:1 was added to the obtained reaction mixture until the mixture was separated into a black layer and a colorless and transparent solution layer, and thereafter a black sample was obtained by centrifugation. The obtained black precipitate was dispersed in water. An operation of adding acetone to the mixture to be separated into a black sample and a colorless and transparent solution again and performing centrifugation of the resultant was repeated three times, thereby obtaining a black sample. The sample is called a catalyst precursor. The catalyst precursor was dried in a vacuum desiccator.

The dried catalyst precursor was pulverized to powder. 500 mg of the precursor powder was moved to a quartz boat, and the temperature thereof was increased to 700° C. in a state where 5% $H_2$—Ar gas was flowed, thereby manufacturing a catalyst.

From the result of the TEM measurement, it was confirmed that the particle diameter of Fe nanoparticles supported in Vulcan (registered trademark) was 13±10 nm. From the result of the powder XRD measurement, it was confirmed that Fe nanoparticles in the manufactured catalyst had a bcc structure. From the result of the ICP-AES measurement, it was confirmed that 13.7 wt % of Fe was contained in the catalyst.

<Manufacture of Propylene by FT Reaction>

Using the FT reaction catalyst obtained in each of the Manufacture Examples and the apparatus illustrated in FIG. 1, the FT reaction was performed in the following order to manufacture propylene.

Example 1

The catalyst obtained in Manufacture Example 1 was subjected to compression molding at 60 MPa for 30 minutes and was granulated to 20 to 40 Mesh. 0.5 g of the obtained FT reaction catalyst was filled in the apparatus, and was subjected to the activation treatment under the conditions of a synthesis gas ($H_2/CO=1/1$, molar ratio) atmosphere (W/F:10 g·h/mol), normal pressure, and 300° C. for 10 hours. Thereafter, the synthesis gas ($H_2/CO=1/1$, molar ratio) was flowed under the conditions of W/F:10 g·h/mol, 1 MPa, and 300° C. for the FT reaction. The reaction time was 6 hours.

The reaction product was analyzed by gas chromatography, and the CO conversion rate and the selectivity of propylene were calculated from the value of a peak area percentage in the obtained spectrum. The results are shown in Table 1.

Example 2

The catalyst obtained in Manufacture Example 2 was subjected to compression molding at 60 MPa for 30 minutes and was granulated to 20 to 40 Mesh. 0.5 g of the obtained FT reaction catalyst was filled in the apparatus, was treated under the conditions of a hydrogen gas atmosphere (W/F:10 g·h/mol), normal pressure, and 400° C. for 10 hours, and was thereafter treated under the conditions of a synthesis gas ($H_2/CO=2/1$, molar ratio) atmosphere (W/F:10 g·h/mol), 1 MPa, and 240° C. for 6 hours. Thereafter, the resultant was further subjected to a treatment under the conditions of a synthesis gas ($H_2/CO=1/1$, molar ratio) atmosphere, normal pressure, and 300° C. for 10 hours. After the series of activation treatments, the synthesis gas ($H_2/CO=1/1$, molar ratio) was flowed under the conditions of W/F:10 g·h/mol, 1 MPa, and 300° C. for the FT reaction. The reaction time was 6 hours.

The reaction product was analyzed by gas chromatography, and the CO conversion rate and the selectivity of propylene were calculated from the value of a peak area percentage in the obtained spectrum. The results are shown in Table 1.

Example 3

The catalyst obtained in Manufacture Example 3 was subjected to compression molding at 60 MPa for 30 minutes and was granulated to 20 to 40 Mesh. 0.5 g of the obtained FT reaction catalyst was filled in the apparatus, and was subjected to the activation treatment under the conditions of a synthesis gas ($H_2/CO=1/1$, molar ratio) atmosphere (W/F:10 g·h/mol), normal pressure, and 300° C. for 10 hours. Thereafter, the synthesis gas ($H_2/CO=1/1$, molar ratio) was flowed under the conditions of W/F:10 g·h/mol, 1 MPa, and 300° C. for the FT reaction. The reaction time was 6 hours.

The reaction product was analyzed by gas chromatography, and the CO conversion rate and the selectivity of propylene were calculated from the value of a peak area percentage in the obtained spectrum. The results are shown in Table 1.

Comparative Example 1

The catalyst obtained in Manufacture Example 4 was subjected to compression molding at 60 MPa for 30 minutes and was granulated to 20 to 40 Mesh. 0.5 g of the obtained FT reaction catalyst was filled in the apparatus, and was subjected to the activation treatment under the conditions of a synthesis gas ($H_2/CO=1/1$, molar ratio) atmosphere, normal pressure, and 300° C. for 10 hours. Thereafter, the synthesis gas ($H_2/CO=1/1$, molar ratio) was flowed under the conditions of W/F:10 g·h/mol, 1 MPa, and 300° C. for the FT reaction. The reaction time was 6 hours.

The reaction product was analyzed by gas chromatography, and the CO conversion rate and the selectivity of propylene were calculated from the value of a peak area percentage in the obtained spectrum. The results are shown in Table 1.

Comparative Example 2

The catalyst obtained in Manufacture Example 5 was subjected to compression molding at 60 MPa for 30 minutes and was granulated to 20 to 40 Mesh. 0.5 g of the obtained FT reaction catalyst was filled in the apparatus, and was subjected to the activation treatment under the conditions of a synthesis gas ($H_2/CO=1/1$, molar ratio) atmosphere, normal pressure, and 300° C. for 10 hours. Thereafter, the synthesis gas ($H_2/CO=1/1$, molar ratio) was flowed under the conditions of W/F:10 g·h/mol, 1 MPa, and 300° C. for the FT reaction. The reaction time was 6 hours.

The reaction product was analyzed by gas chromatography, and the CO conversion rate and the selectivity of propylene were calculated from the value of a peak area percentage in the obtained spectrum. The results are shown in Table 1.

Example 4

0.5 g of the catalyst obtained in the same manner as in Manufacture Example 2 was filled in the apparatus, was treated under the conditions of a hydrogen gas atmosphere (50 ml/min), normal pressure, and 400° C. for 5 hours, and was thereafter treated under the conditions of a synthesis gas ($H_2/CO=1/1$, molar ratio) atmosphere (37.3 ml/min), 1 MPa, and 260° C. for 5 hours. Thereafter, the resultant was further treated under the conditions of a synthesis gas ($H_2/CO=1/1$, molar ratio) atmosphere (37.3 ml/min), normal pressure, and 300° C. for 5 hours. After the series of activation treatments, the synthesis gas ($H_2/CO=1/1$, molar ratio) was flowed under the conditions of W/F:5 g·h/mol, 1 MPa, and 300° C. for the FT reaction. The reaction time was 14 hours.

The reaction product was analyzed by gas chromatography, and the CO conversion rate and the selectivity of propylene were calculated from the value of a peak area percentage in the obtained spectrum. The results are shown in Table 1.

TABLE 1

| | CO conversion rate (%) | Selectivity of propylene (%) |
|---|---|---|
| Example 1 | 40 | 8 |
| Example 2 | 64 | 16 |
| Example 3 | 50 | 3 |
| Example 4 | 87 | 21 |
| Comparative Example 1 | 12 | 4 |
| Comparative Example 2 | 27 | 12 |

As is apparent from Table 1, the CO conversion rates in Examples 1 to 4 were significantly higher than those in Comparative Examples 1 and 2, since the alloy nanoparticles made of iron and cobalt were used, a higher synergistic effect on the improvement in the CO conversion rate was obtained rather than that in a case where iron or cobalt was used singly. Among these, the selectivity of propylene in Examples 2 and 4 was particularly superior.

Manufacture of Zeolite Catalyst

Manufacture Example 6

To a solution containing 6.507 g of a 10% by mass tetrapropylammonium hydroxide aqueous solution, 0.029 g of aluminum nitrate nonahydrate, 0.010 g of barium acetate, 8.544 g of ion-exchanged water, and 1.968 g of ethanol, 2.250 g of tetraethyl orthosilicate was gradually added and violently stirred to form a uniform sol, followed by hydrothermal synthesis at 180° C. for 24 hours.

After drying the obtained precipitate at 120° C., the resultant was calcined at a high temperature of 550° C. for 5 hours, thereby obtaining 0.603 g of BaZSM-5 ($SiO_2/Al_2O_3/BaO=280/1/1$) as a zeolite.

As a result of the ICP analysis, the ratio (molar ratio) of the contents of oxides of the obtained zeolite was $SiO_2/Al_2O_3/BaO=306/1.00/1.05$.

<Manufacture of Propylene by FT Reaction and Cracking Treatment>

Using the FT reaction catalyst and the zeolite catalyst described in the Manufacture Examples and the apparatus illustrated in FIG. 2, the FT reaction and the cracking treatment were performed in the following order to manufacture propylene.

Example 5

0.5 g of the FT reaction catalyst obtained in the same manner as in Manufacture Example 2 was filled in the first reactor, and 0.3 g of the BaZSM-5 obtained in the same manner as in Manufacture Example 6 as a cracking catalyst was filled in the second reactor. The FT reaction catalyst was treated under the conditions of a hydrogen gas atmosphere (W/F: 5 g·h/mol with respect to the FT reaction catalyst), normal pressure, and 400° C. for 12 hours, and was treated under the conditions of a synthesis gas ($H_2/CO=2/1$, molar ratio) atmosphere (W/F: 5 g·h/mol with respect to the FT reaction catalyst), 1 MPa, and 240° C. for 12 hours. Subsequently, the resultant was further treated under the conditions of a synthesis gas ($H_2/CO=1/1$, molar ratio) atmosphere (W/F: 5 g·h/mol with respect to the FT reaction catalyst), normal pressure, and 300° C. for 12 hours. After the series of activation treatments, the synthesis gas ($H_2/CO=1/1$, molar ratio) was flowed under the conditions of W/F:10 g·h/mol, 1 MPa, and 300° C. for the FT reaction of the FT reaction catalyst. The reaction time was 16 hours.

The product of the FT reaction was flowed in the second reactor under the conditions of 0.1 MPa and 500° C. for the cracking treatment. The cracking treatment was started simultaneously with the FT reaction, and the treatment time thereof was 6 hours.

The product obtained by the cracking treatment was analyzed by gas chromatography, and the CO conversion rate and the selectivity of propylene were calculated from the value of a peak area percentage in the obtained spectrum. The results are shown in Table 2.

TABLE 2

| | CO conversion rate (%) | Selectivity of propylene (%) |
|---|---|---|
| Example 5 | 33 | 28 |

As is apparent from Table 2, in Example 5, in addition to a high CO conversion rate, the selectivity of propylene was also excellent, and thus the amount of the light olefin having 2 to 4 carbon atoms in the product was significantly high.

The present invention can be used for the manufacture of a light olefin having 2 to 4 carbon atoms such as propylene using the FT reaction.

DESCRIPTION OF REFERENCE NUMERALS AND CHARACTERS 1, 2 . . . manufacturing apparatus, 10 . . . FT reaction catalyst, 11 . . . reactor, 12 . . . first pipe, 13 . . . second pipe, 21 . . . first reactor, 22 . . . first pipe, 23 . . . second pipe, 24 . . . back pressure valve, 25 . . . second reactor, 26 . . . third pipe, 27 . . . synthesis gas supply means While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A method of manufacturing an olefin having 2 to 4 carbon atoms, comprising:
   reacting a catalyst with synthesis gas through a Fischer-Tropsch reaction, thereby obtaining the olefin having 2 to 4 carbon atoms,
   wherein the catalyst is a catalyst obtained by reducing an iron ion and a cobalt ion in a dispersion liquid or a solution containing the iron ion, the cobalt ion and a dispersant that interacts with the iron ion and the cobalt ion.

2. The method of manufacturing an olefin having 2 to 4 carbon atoms according to claim 1,
   wherein a molar ratio of iron and cobalt in the catalyst is 20:80 to 80:20.

3. The method of manufacturing an olefin having 2 to 4 carbon atoms according to claim 1,
   wherein 50% or more of the total number of granular particles of the catalyst have particle diameters of 1 to 50 nm.

4. The method of manufacturing an olefin having 2 to 4 carbon atoms according to claim 1,
   wherein the catalyst further includes a carbon support.

5. The method of manufacturing an olefin having 2 to 4 carbon atoms according to claim 1,
   wherein the Fischer-Tropsch reaction is a gas-phase reaction.

6. A method of manufacturing propylene, comprising:
   reacting a catalyst with synthesis gas through a Fischer-Tropsch reaction, thereby obtaining propylene,
   wherein the catalyst is a catalyst obtained by reducing an iron ion and a cobalt ion in a dispersion liquid or a solution containing the iron ion, the cobalt ion and a dispersant that interacts with the iron ion and the cobalt ion.

7. The method of manufacturing an olefin having 2 to 4 carbon atoms according to claim 4,
wherein the carbon support is carbon black.

8. The method of manufacturing propylene according to claim 6,
wherein the molar ratio of the iron ion and the cobalt ion is 20:80 to 80:20.

9. The method of manufacturing an olefin having 2 to 4 carbon atoms according to claim 1,
wherein the catalyst is a catalyst obtained by reducing an iron ion and a cobalt ion in a solution containing the iron ion, the cobalt ion and a dispersant that interacts with the iron ion and the cobalt ion.

* * * * *